United States Patent
Luedi

(10) Patent No.: US 12,295,594 B2
(45) Date of Patent: *May 13, 2025

(54) NON-ROTATIONAL BONE CUTTING TOOLS AND RELATED SYSTEMS AND METHODS

(71) Applicant: Medtronic Xomed, Inc., Jacksonville, FL (US)

(72) Inventor: Manfred K. Luedi, Jacksonville, FL (US)

(73) Assignee: Medtronic Xomed, Inc., Jacksonville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 18/620,902

(22) Filed: Mar. 28, 2024

(65) Prior Publication Data

US 2024/0260971 A1    Aug. 8, 2024

Related U.S. Application Data

(63) Continuation of application No. 17/515,862, filed on Nov. 1, 2021, now Pat. No. 11,957,361.

(Continued)

(51) Int. Cl.
  *A61B 17/16* (2006.01)
  *A61B 17/00* (2006.01)

(52) U.S. Cl.
  CPC ...... *A61B 17/1628* (2013.01); *A61B 17/1615* (2013.01); *A61B 17/1626* (2013.01);
  (Continued)

(58) Field of Classification Search
  CPC . A61B 17/16; A61B 17/1613; A61B 17/1615; A61B 17/1617; A61B 17/162;
  (Continued)

(56) References Cited

U.S. PATENT DOCUMENTS 5,026,387 A    6/1991   Thomas
6,579,244 B2   6/2003   Goodwin
(Continued)

FOREIGN PATENT DOCUMENTS

CN    101674782 A    3/2010
CN    110114021 A    8/2019
(Continued)

OTHER PUBLICATIONS

Application and File History for U.S. Appl. No. 17/516,131, filed Nov. 1, 2021. Inventor: Luedi.
(Continued)

*Primary Examiner* — Eric S Gibson
(74) *Attorney, Agent, or Firm* — Husch Blackwell LLP

(57) ABSTRACT

A surgical instrument employs a mass-spring system to drive the periodic reversal of the rotational direction of a bone dissection head. The instrument comprises a housing, a harmonic oscillator contained in the housing, an output member at least partially received in the housing and configured to be driven by the harmonic oscillator to reversibly rotate about a longitudinal axis in alternating directions, a dissection head having an attachment portion configured to be selectively driven in alternating rotational directions by the output member to remove material from a target bone, and a controller operable to initiate and stop the harmonic oscillator.

15 Claims, 9 Drawing Sheets

Related U.S. Application Data

(60) Provisional application No. 63/119,987, filed on Dec. 1, 2020.

(52) U.S. Cl.
CPC ............ *A61B 2017/00477* (2013.01); *A61B 2017/00876* (2013.01); *A61B 17/1695* (2013.01)

(58) Field of Classification Search
CPC ............ A61B 17/1622; A61B 17/1624; A61B 17/1626; A61B 17/1628; A61B 17/1695
See application file for complete search history.

(56) References Cited

U.S. PATENT DOCUMENTS

| | | | |
|---|---|---|---|
| 9,554,807 B2 | 1/2017 | McGinley et al. | |
| 9,561,544 B2 | 2/2017 | Walsh et al. | |
| 9,788,851 B2 | 10/2017 | Dannaher et al. | |
| 9,855,060 B2* | 1/2018 | Ardel | A61B 17/162 |
| 9,936,961 B2 | 4/2018 | Chien et al. | |
| 10,194,922 B2* | 2/2019 | Bono | A61B 17/1624 |
| 10,194,966 B2 | 2/2019 | Corpa de la Fuente | |
| 10,390,895 B2 | 8/2019 | Henderson et al. | |
| 10,531,929 B2 | 1/2020 | Widenhouse et al. | |
| 10,588,645 B1* | 3/2020 | Cao | A61B 17/320068 |
| 11,103,256 B2* | 8/2021 | Akbarian | A61B 17/1688 |
| 11,957,361 B2* | 4/2024 | Luedi | A61B 17/1622 |
| 11,986,192 B2 | 5/2024 | Luedi | |
| 2004/0058636 A1 | 3/2004 | Hinsch et al. | |
| 2004/0092992 A1 | 5/2004 | Adams et al. | |
| 2004/0122460 A1 | 6/2004 | Shores et al. | |
| 2006/0178672 A1 | 8/2006 | Shores et al. | |
| 2013/0060278 A1 | 3/2013 | Bozung | |
| 2013/0282038 A1 | 10/2013 | Dannaher et al. | |
| 2013/0304069 A1* | 11/2013 | Bono | A61B 17/1671 606/80 |
| 2014/0239600 A1 | 8/2014 | Walsh et al. | |
| 2014/0262408 A1* | 9/2014 | Woodard | A61B 17/1637 173/217 |
| 2015/0018815 A1* | 1/2015 | Sartor | A61B 17/32053 606/171 |
| 2015/0342618 A1* | 12/2015 | Nguyen | A61C 8/0092 433/27 |
| 2016/0066972 A1 | 3/2016 | Corpa de la Fuente | |
| 2018/0049820 A1 | 2/2018 | Widenhouse et al. | |
| 2018/0049822 A1 | 2/2018 | Henderson et al. | |
| 2018/0168757 A1* | 6/2018 | Bono | A61B 34/30 |
| 2018/0185052 A1 | 7/2018 | Zhou et al. | |
| 2019/0142439 A1* | 5/2019 | Collerais | A61B 17/1617 606/80 |
| 2019/0350597 A1* | 11/2019 | Akbarian | A61B 17/24 |
| 2021/0137548 A1* | 5/2021 | Vogt | A61B 17/3203 |
| 2022/0160373 A1 | 5/2022 | Luedi | |
| 2022/0167996 A1* | 6/2022 | Luedi | A61B 17/1615 |
| 2022/0218421 A1 | 7/2022 | Junio et al. | |
| 2024/0260971 A1* | 8/2024 | Luedi | A61B 17/1628 |
| 2024/0260972 A1 | 8/2024 | Luedi | |

FOREIGN PATENT DOCUMENTS

| | | | | |
|---|---|---|---|---|
| CN | 111281479 A | 6/2020 | | |
| CN | 111655186 A | 9/2020 | | |
| DE | 102010014148 A1 | 10/2011 | | |
| EP | 4005509 A1 | 6/2022 | | |
| WO | WO 2013/029039 A1 | 2/2013 | | |
| WO | WO-2013169456 A1 * | 11/2013 | ........... | A61B 17/162 |
| WO | WO 2016/037066 A1 | 3/2016 | | |
| WO | WO-2019224631 A1 * | 11/2019 | ........ | A61B 17/1615 |

OTHER PUBLICATIONS

Application and File History for U.S. Appl. No. 17/515,862, filed Nov. 1, 2021. Inventor: Luedi.
International Search Report and Written Opinion corresponding to PCT/US2021/061439, mailed Apr. 19, 2022, 13 pgs.
International Preliminary Report on Patentability from PCT Application PCT/US2021/061439, date Jun. 15, 2023, 9 pgs.
Chinese Search Report corresponding to Application No. 202180081179.6, dated Dec. 6, 2024.

* cited by examiner

NON-ROTATIONAL BONE CUTTING TOOLS AND RELATED SYSTEMS AND METHODS

CROSS-REFERENCE TO RELATED APPLICATION

This application is a continuation of U.S. application Ser. No. 17/515,862 filed Nov. 1, 2021, which claims the benefit of U.S. Provisional Patent Application No. 63/119,987 filed Dec. 1, 2020, the entire disclosures of which are incorporated by reference herein.

FIELD

The present disclosure generally relates to surgical instruments for use in the dissection of bone and other tissue. More particularly, the present disclosure relates to surgical instruments with alternating rotary motion.

BACKGROUND

In various surgical procedures, it is necessary to dissect bone or other tissue. Many conventional surgical instruments used for the dissection of bone or other tissue employ pneumatic or electrical motors to rotate a cutting element. In their most basic form, such surgical instruments comprise a motor portion having a rotary shaft, a dissection tool having a cutting or abrading element that is moved by the rotating shaft of the motor, and a coupling arrangement for connecting the dissection tool to a spindle or collet of the rotary shaft. The spindle or collet of the rotary shaft is usually housed within a base that is attached to the motor.

Bone drilling is performed in many surgical procedures in orthopedic surgery as well as in the fields of neurosurgery, plastic surgery, and otorhinolaryngology. For example, in surgery to fixate fractured bones after a trauma, implants like nails, plates, screws, and wire are used and these implants are inserted into holes made by drilling cylindrical tunnels into the bone. Risks during the drilling procedure include harm caused to the bone, muscle, nerves, and venous tissues by the high temperatures which can be generated by the high-speed rotation of the drill bit; the rapidly rotating drill becoming wrapped by the surrounding tissue in an uncontrolled manner; or if the drill bit does not stop immediately after it exits the second cortex of the bone. Of these issues, the damage due to heat typically has received the most attention. High speeds are desired for safe and effective surgery but can lead to significant heat from friction both at the cutting site, which can cause bone necrosis, and in the body of the drill and attachments. Heat generated in the drill itself can cause the surface to heat as well, which can burn patient tissues away from the cutting site. Heat damage is acknowledged as a major risk to surrounding tissue and has been extensively addressed in the art.

While known surgical tools include various measures to limit the damage to surrounding tissue, a need exists in the pertinent art for an improved surgical tool which limits the risk of force damage to surrounding tissue due to becoming wrapped around the drill bit or around the exposed shaft of the spinning cutting tool.

SUMMARY

The techniques of this disclosure generally relate to bone dissection tools, and particularly to tools to limit collateral damage to nerve and other tissue surrounding the bone.

Embodiments of the present disclosure can comprise a housing, a harmonic oscillator contained in the housing, an output member at least partially received in the housing and configured to be driven by the harmonic oscillator to reversibly rotate about a longitudinal axis in alternating directions, a dissection head having an attachment portion configured to be selectively driven in alternating rotational directions by the output member to remove material from a target bone, and a controller operable to initiate and stop the harmonic oscillator.

In another aspect of the present disclosure, a surgical instrument can comprise a housing, a motor contained in the housing, an output member at least partially received in the housing and configured to be driven by the motor to reversibly rotate about a longitudinal axis in alternating directions, a dissection head having an attachment portion configured to be selectively driven in alternating rotational directions by the output member to remove material from a target bone, and a controller operable to initiate and stop the motor.

In embodiments, the present disclosure can comprise a surgical instrument for the dissection of bone or other tissue. The surgical instrument can comprise a mass spring oscillator having an alternating rotational output, a tool having a shaft with a dissection area disposed adjacent to a distal end and a coupling area disposed adjacent to an opposite proximal end, and a coupling assembly configured to selectively couple the alternating rotational output to the coupling area of the tool in a run position. The coupling assembly can include an unlocked position to decouple the tool from the alternating rotational output, further including an actuator for controlling movement of the coupling assembly from the run position to the unlocked position.

In embodiments, the present disclosure provides for a method of operating a bone drill with alternating bidirectional rotation. The method can comprise determining a set of parameters associated with a procedure to be performed, determining an optimum frequency according to the set of parameters, wherein the optimum frequency is associated with a desired speed of operation of the bone drill, determining an optimum range of rotation according to the set of parameters, wherein the range of rotation is associated with a degree of rotation between reversals of the bone drill, and configuring the bone drill to operate at the optimum frequency and the optimum range of rotation.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The disclosure can be more completely understood in consideration of the following detailed description of various embodiments of the disclosure, in connection with the accompanying drawings, in which.

Figure 1:
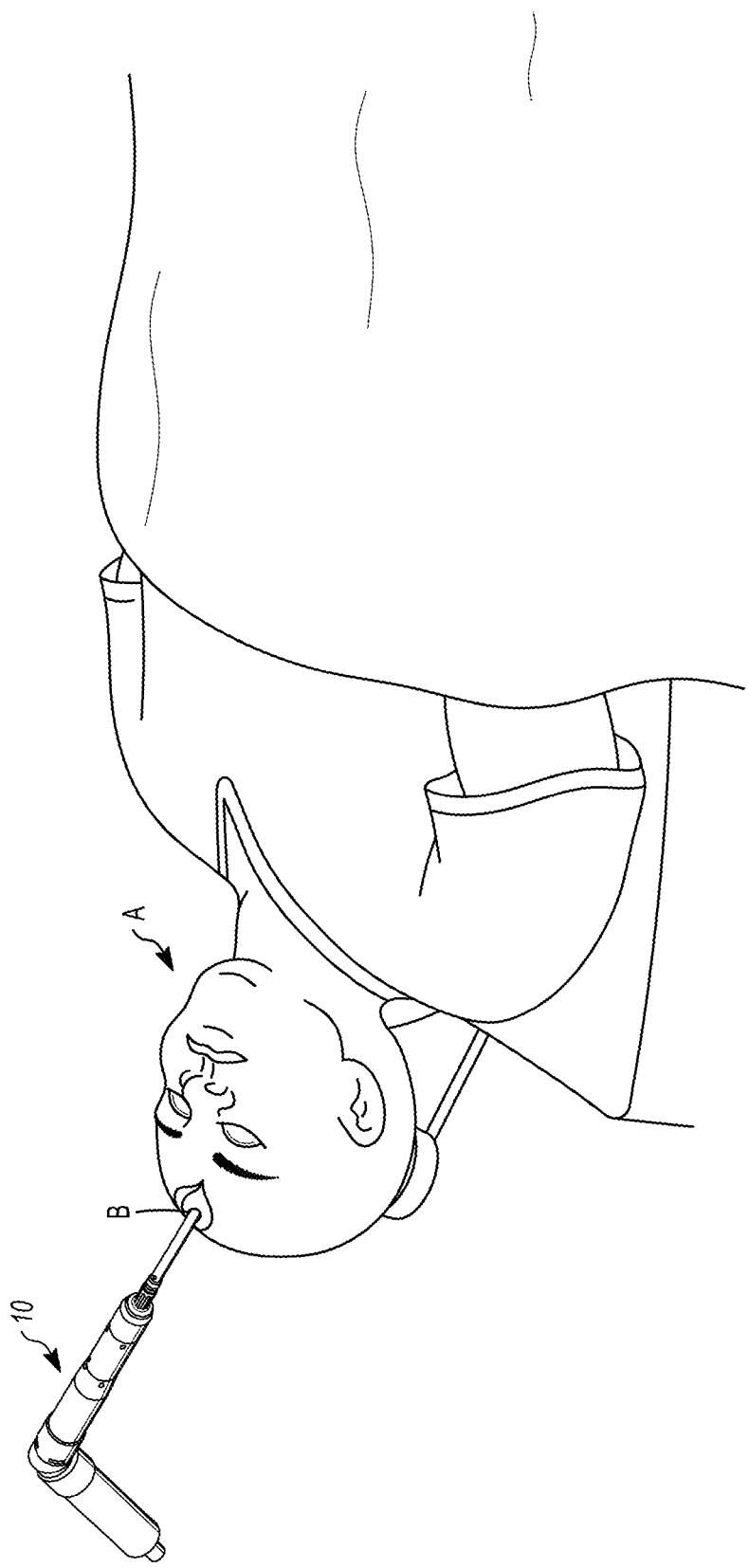
FIG. 1 is an illustration of a surgical dissection tool according to the present disclosure used in a human patient, according to embodiments of the present disclosure.
Figure 2A:
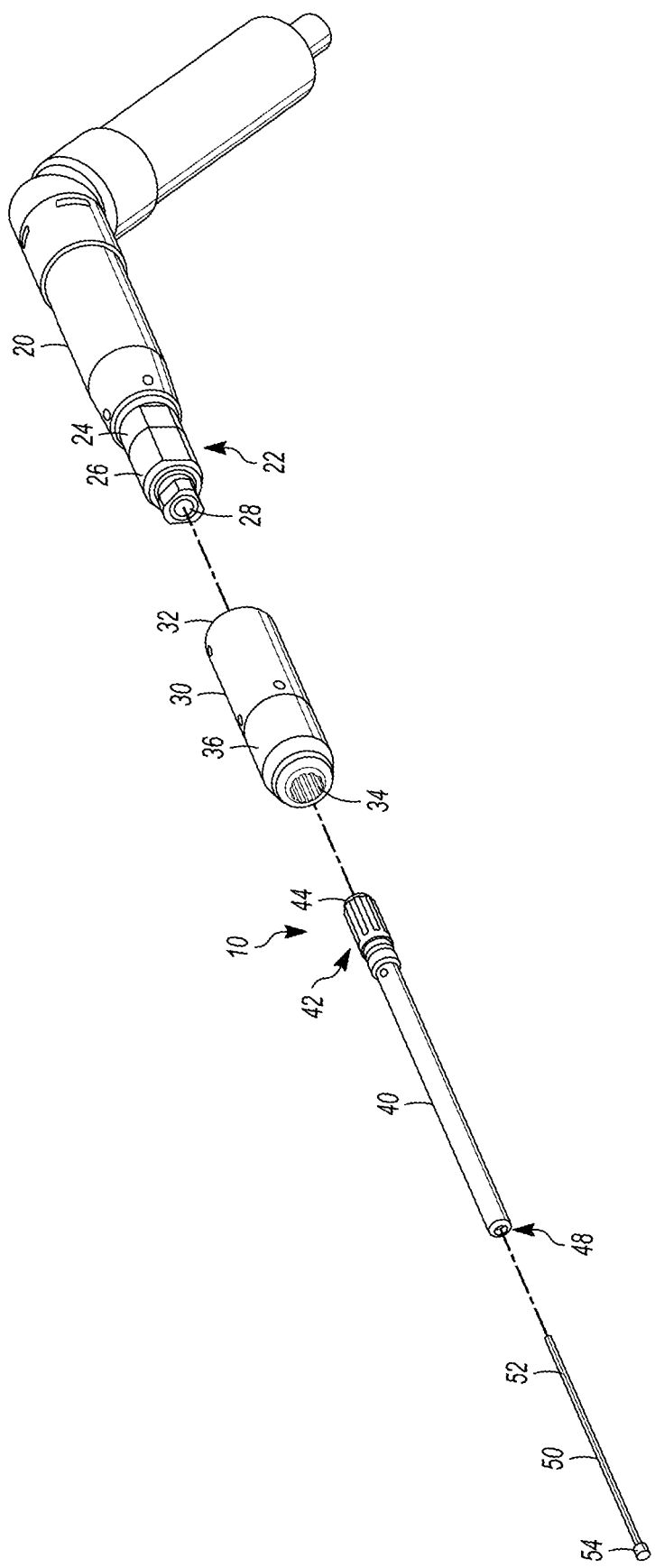
FIG. 2A is a partially exploded perspective view of an embodiment of a surgical dissection tool, according to embodiments of the present disclosure.
Figure 2B:
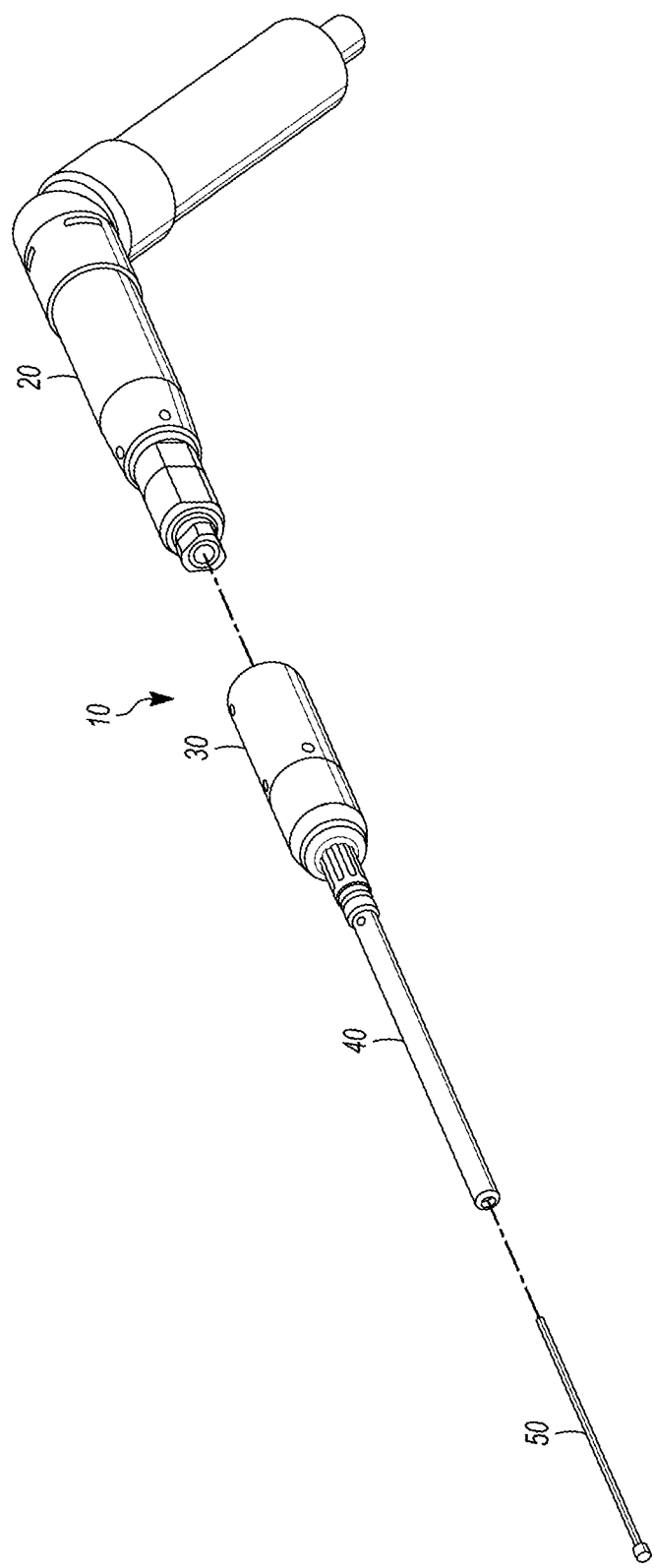
FIG. 2B is a partially exploded perspective view of the embodiment of FIG. 2A, according to embodiments of the present disclosure.
Figure 2C:
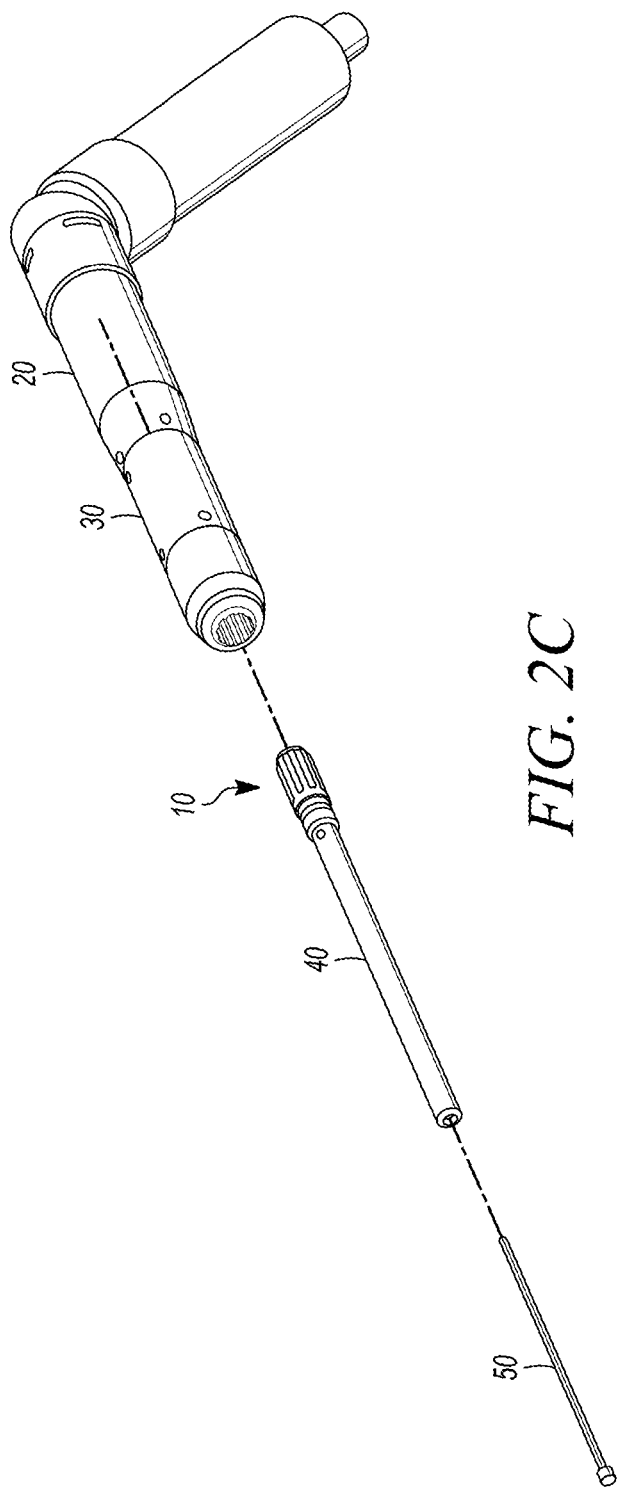
FIG. 2C is a partially exploded perspective view of the embodiment of FIG. 2A, according to embodiments of the present disclosure.
Figure 2D:
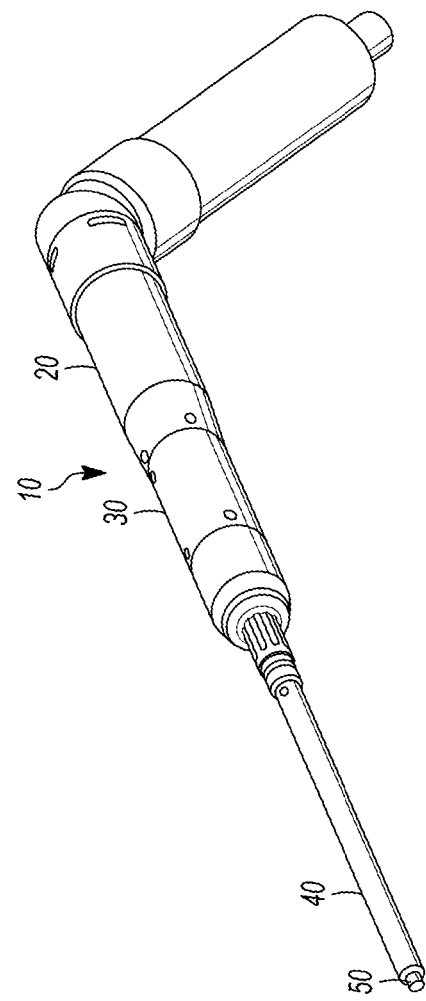
FIG. 2D is an assembled perspective view of the embodiment of FIG. 2A, according to embodiments of the present disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

The following description of various embodiments is merely exemplary in nature and is in no way intended to limit the disclosure, its application, or uses.

Much of the art dedicated to limiting force damage to tissue wrapped around involves the integration of guards or deflectors to prevent the spinning drill tip from contacting and becoming entangled in non-target tissue. However, as surgery continually evolves to be less invasive, there is continuing pressure to streamline surgical tools. Further, drills and other surgical cutting tools are being used in increasingly confined spaces or in increasing proximity to sensitive tissue, for instance in spinal surgeries, or limiting the effectiveness of any protruding features.

Disclosed herein is a rotary cutting tool or drill configured for bidirectional alternating rotation of the head. This bidirectional movement of the rotary head can release or prevent wrapping of tissue by continually reversing the direction of rotation.

In one particular embodiment, the surgical instrument employs a mass-spring system to drive the periodic reversal of the rotational direction. Use of a mass-spring system permits operation with less power input than conventional tools leading to better energy efficiency. In addition to the minimal energy input needed to start the motion due to the storage of energy by the spring, the need to overcome motor inertia to stop the motion is not present. The instrument can comprise a housing, a harmonic oscillator contained in the housing, an output member at least partially received in the housing and configured to be driven by the harmonic oscillator to reversibly rotate about a longitudinal axis in alternating directions, a dissection head having an attachment portion configured to be selectively driven in alternating rotational directions by the output member to remove material from a target bone, and a controller operable to initiate and stop the harmonic oscillator.

Referring now to FIG. 1, there is shown a human patient A undergoing a neurological operation. As is common practice, access to the brain or other neurological structures often requires delicate dissection of bone and other tissues B to gain access. By way of example, dissection tool assembly 10 in accordance with one aspect of the present disclosure is shown being utilized to dissect a portion of patient A's bone and other tissue B adjacent to the surgical access site.

Referring now to FIGS. 2A through 2D, an example dissection tool assembly 10 for the dissection of bone or other tissue is illustrated. A pneumatic motor 20 is illustrated having a collet assembly 22 disposed on a distal end of pneumatic motor 20. Collet assembly 22 can include a proximal movable portion 24 and a distal fixed portion 26. A shaft receiving aperture 28 on the distal end can slidably receive a rotary shaft. The dissection tool assembly 10 can further include an attachment base coupling assembly 30 adapted to be received about collet assembly 22 and having an attachment aperture 34 at its distal length. An attachment tube 40 can be provided having a proximal portion 42 with grooves 44 extending along a portion thereof. The distal end of attachment tube 40 can include a tool receiving aperture 48. Coupling assembly 30 and attachment tube 40 can be combined to form a telescoping attachment assembly 12. An exemplary illustration of a dissection tool 50 is also shown. Dissection tool 50 can include an elongated shaft 52 and a tissue dissection head 54.

In embodiments, the device 10 can be a handheld device or fully or partially machine-operated or robotic.

Pneumatic motor 20 can be excluded in embodiments, with a mass-spring drive system driving the rotation of dissection head 54. In embodiments, the mass-spring drive system can be provided in addition to a motor, such as pneumatic motor 20, and a clutch can be integrated to provide for changing between continuous rotation driven by the motor and alternating rotation driven by the mass-spring system or changing among varying mass-spring systems, e.g., systems with varying frequencies.

In embodiments a device 10 according to the present disclosure can comprise one, two, or more mass-spring systems, selectable via a clutch, configured to drive a dissection head at different frequencies or at different degrees of rotation. For example, the mass-spring system and the dissection head can be configured for the dissection head to rotate just one or two degrees, or more than two degrees, such as 5 degrees or more, 10 degrees or more, 15 degrees or more, 30 degrees or more, 45 degrees or more, 90 degrees or more, 120 degrees or more, 180 degrees or more, 360 degrees or more, 720 degrees or more, etc., before reversing and rotating fully back to the initial position, such that the dissection head alternates rotating an equal number of degrees in each direction (clockwise and counterclockwise). Each of the mass-spring systems produces alternating bidirectional rotation of the dissection head at the natural frequency of the mass-spring system.

Figure 3A:
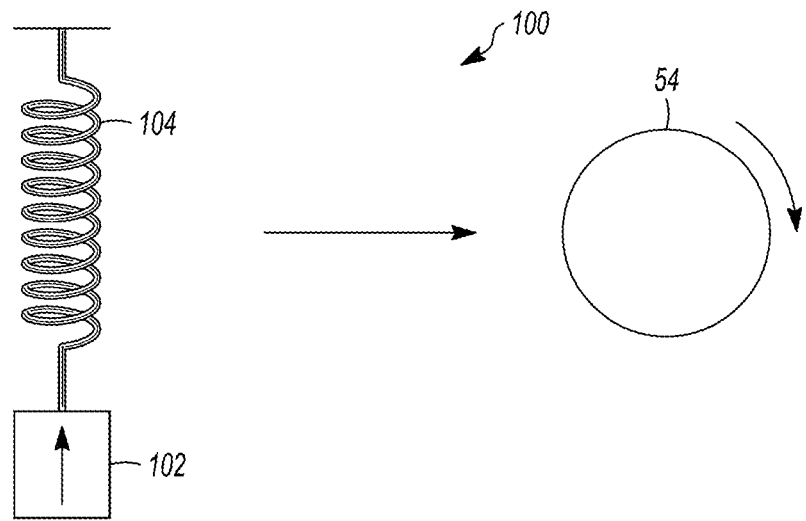
FIG. 3A is a diagram showing a relationship between a simple mass-spring system and alternating rotational motion of a tool, according to embodiments of the present disclosure.
Figure 3A:
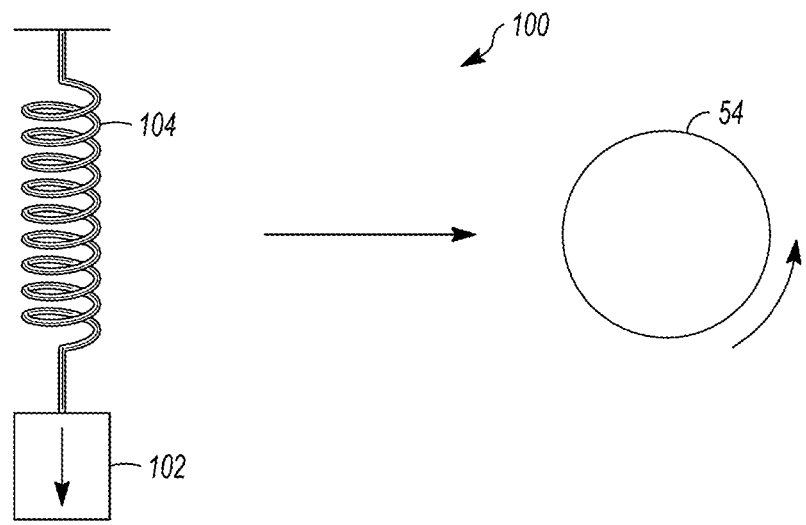
Figure 3B:
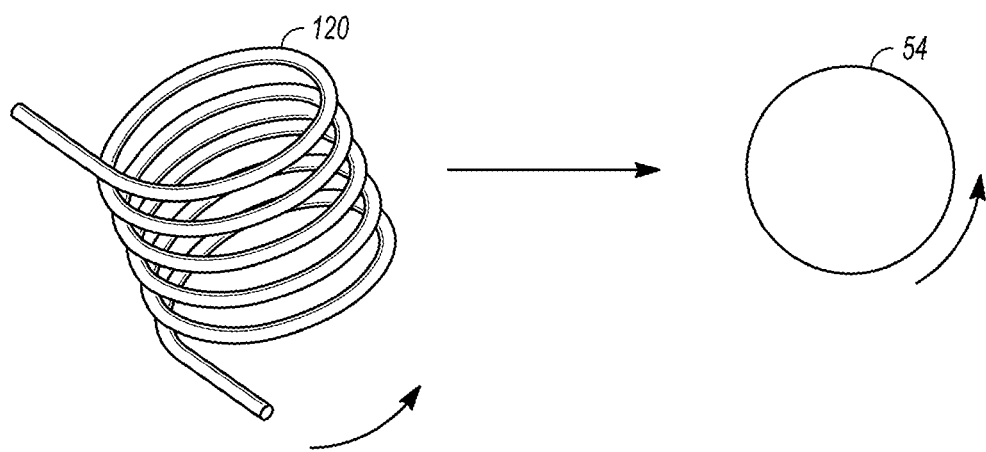
FIG. 3B is a diagram showing a relationship between a torsional spring system and alternating rotational motion of a tool, according to embodiments of the present disclosure.
Figure 3B:
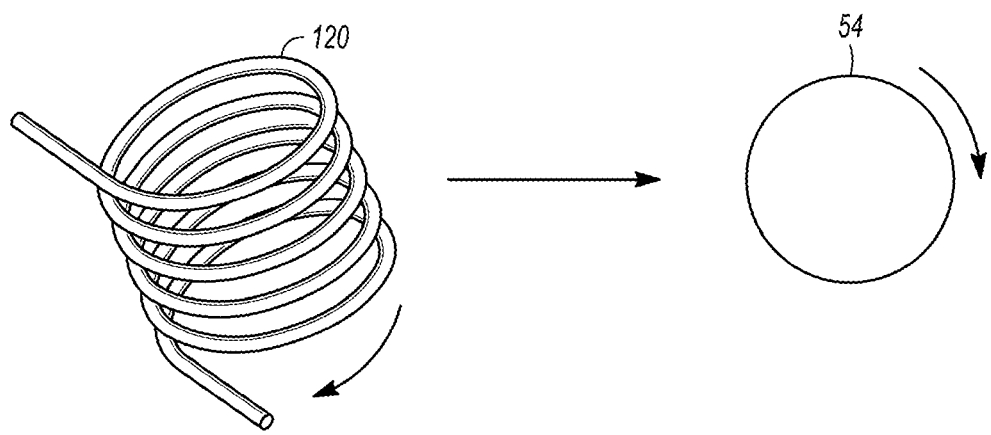

Referring now to FIGS. 3a-3b, a simple example of an alternating rotary dissection head 54 driven by a mass-spring system 100 is shown, according to embodiments of the present disclosure. Mass-spring system 100 can comprise at least mass 102 and spring 104. Mass 102 oscillates on spring 104 at a natural frequency according to the weight of the mass 102 and the stiffness of the spring 104. As mass-spring system 100 moves in a first direction, it drives the dissection head 54 in a first direction, when the spring 104 reaches full extension and oscillates in the return direction, the mass-spring system 100 drives the dissection head 54 in the opposite direction.

Figure 3C:
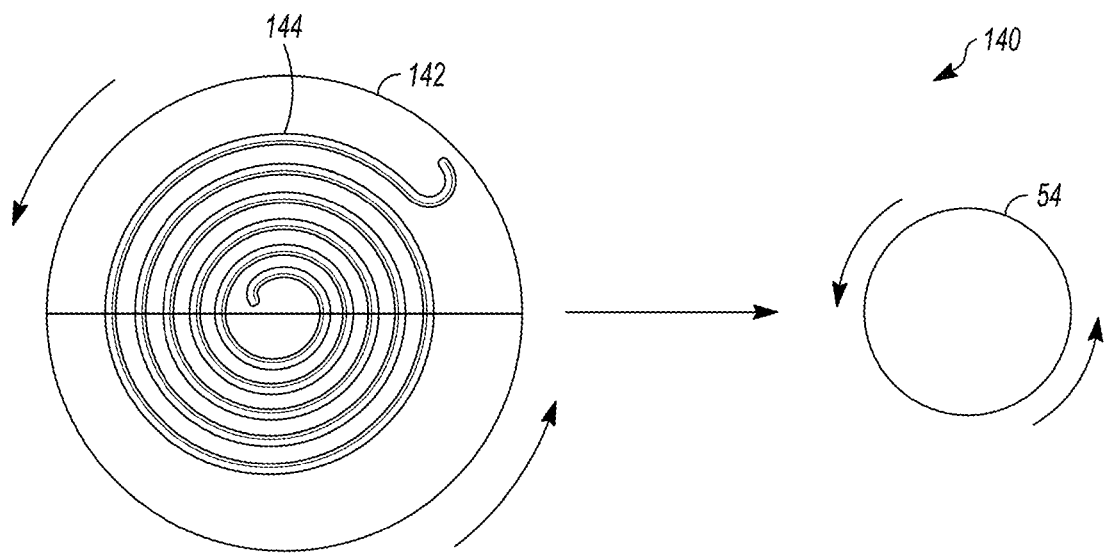
FIG. 3C is a diagram showing a relationship between a simple torsional oscillator and alternating rotational motion of a tool, according to embodiments of the present disclosure.

The mass-spring system can be configured to directly drive the dissection head 54, such as by the use of a torsional spring, such as torsional spring 120 of FIG. 3b. Torsional oscillator 140 of FIG. 3c, where the mass of the balance wheel 142 in combination with a very elastic torsional spring 144 enables a relatively constant period despite energy loss of the system over time. In embodiments, the alternating rotation motion can be achieved by two mass-spring systems. In embodiments, the alternating rotational motion can be achieved by the application of a magnetic field to a linear mass-spring system. In embodiments, a mass-spring system can comprise a single mass and two or more springs, each of the two or more springs producing a different harmonic frequency with the single mass depending on the characteristics, such as stiffness, of the spring.

Figure 3D:
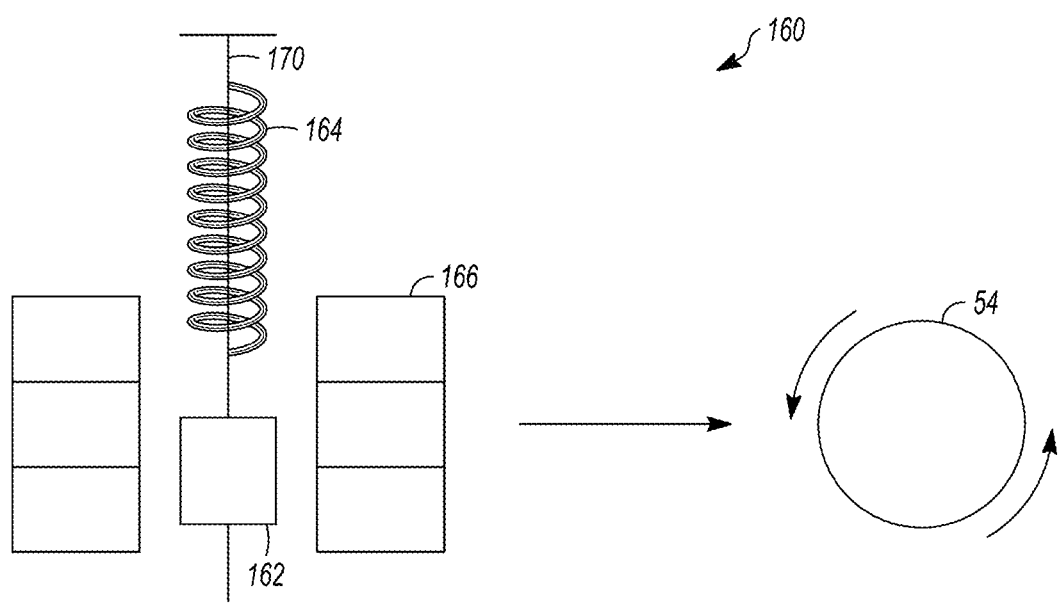
FIG. 3D is a diagram showing a relationship between a simple mass-spring system with a magnetic field applied and alternating rotational motion of a tool, according to embodiments of the present disclosure.

FIG. 3d shows an example embodiment of a mass spring system using a magnetic field. A mass 162 can be made of a magnetic substance and oriented on a shaft 170. A coil 166 is provided around mass 162. Between one end face of mass 162 and housing, a spring 164 can be oriented. When coil 166 has no current flowing through it, mass 162 remains stationary. When coil 166 has an alternating current flowing therethrough, mass 162 moves in alternating directions along shaft 170 in response the a shifting magnetic field, so that by flowing an alternating current through coil 166, mass 162 can be driven to reciprocate axially, thus enabling controlling of the reciprocating motion by a coil current.

In embodiments, an air gap between an outer peripheral surface of mass 162 and inner peripheral surfaces of coil 166 can be made non-uniform in a revolution direction. When the gap between mass 162 and coil 166 changes in revolution direction with changing stroke positions, mass 162 can have a revolution directional force with axial movements thereof, thus obtaining a rectilinear motion as well as a revolutionary motion simultaneously. By altering the magnetic field, mass 162 can be configured to obtain an alternating revolutionary motion.

Varying spring and mass combinations are possible to achieve varying frequencies and ranges of alternating rotation. The frequency for a given procedure can be chosen depending on numerous factors, including the character of the bone, the geometry of the tip, the angle of displacement or contact with the target surface, the rotational speed of the dissection head, etc.

A device 10 according to embodiments of the present disclosure can comprise one or more mass-spring systems. A device 10 comprising multiple mass-spring systems can be configured such that each of the mass-spring systems is configured for a different frequency. A device 10 comprising multiple mass-spring systems can be further configured such that an operator can selectively engage each of the multiple mass-spring systems individually, depending on the desired frequency of alternating rotation.

In embodiments, the mass-spring system can be excluded and other ways of driving the alternating rotational motion of the dissection head can be used. For example, a motor, such as pneumatic motor 20, can be configured to selectively engage a cam or other gearing system to transform the rotational motion of the motor into alternating rotary motion.

The above description has been directed to a coupling assembly 30 that is detachable from motor 20, however; it is contemplated and hereby disclosed that coupler 30 can be integrated with motor 20 in a substantially integral unit. Still further, attachment tube 40 and dissection tool 50 have been shown as substantially straight components. It will be appreciated and is hereby disclosed that attachment tube 40 can be curved to accommodate various applications. It being understood that dissection tool 50 can have sufficient flexibility to conform to the curvature of the attachment along its length.

Figure 4:
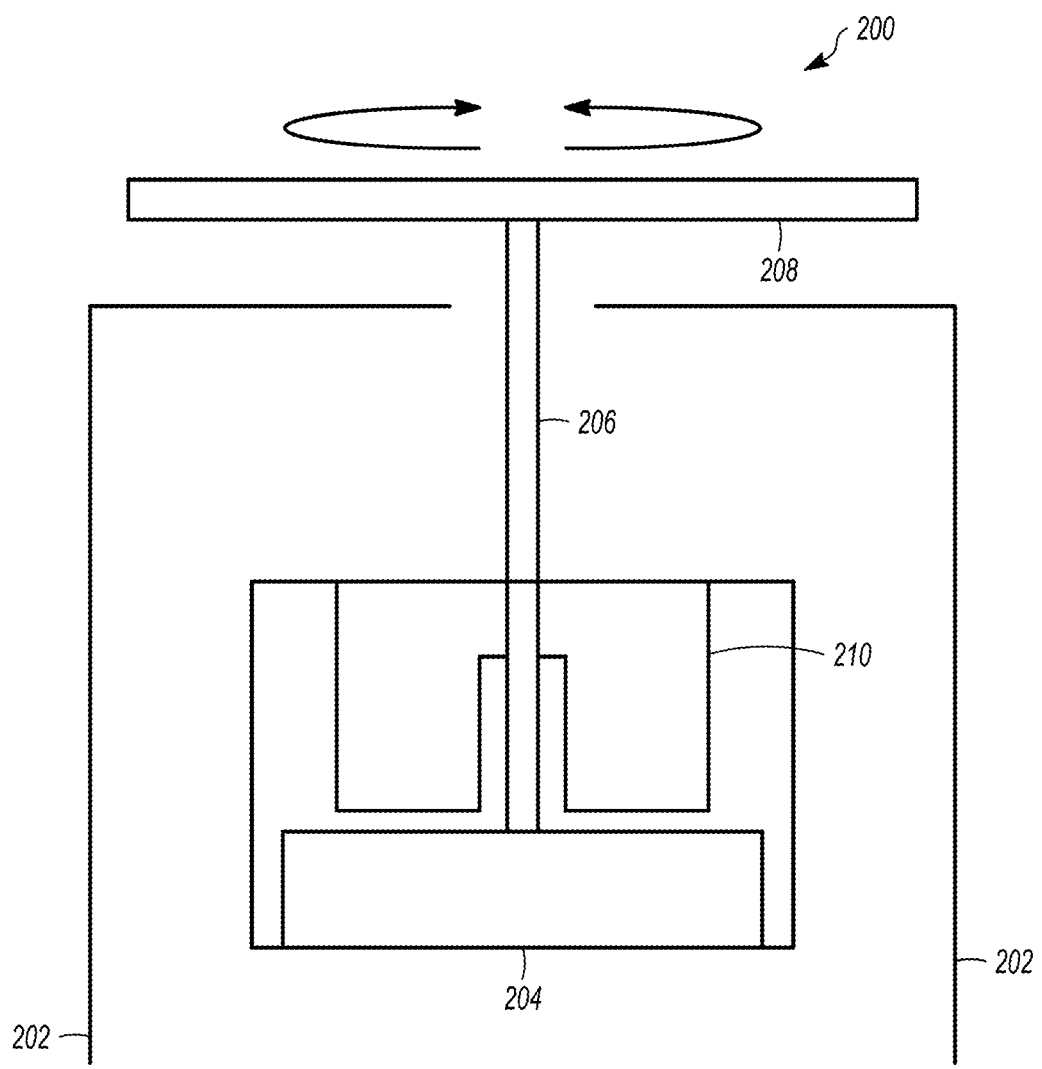
FIG. 4 is a schematic showing operational features of a surgical tool, according to embodiments of the present disclosure.

A simplified example device 200 is illustrated schematically in FIG. 4, according to embodiments of the present disclosure. Device 200 includes a housing 202 which can be held in a user's hand or manipulated robotically. In embodiments, housing 202 can be integrated with a surgical robot. Housing 202 can contain a mass-spring oscillator 204, which can be one or more such oscillators contained in the housing.

Oscillator 204 can be any known oscillator, such as the various mass spring oscillators discussed herein. In embodiments with multiple oscillators 204, device 200 can further include a clutch system for engaging and disengaging the various oscillators. The clutch system can be configured for desired operations, such as ease, speed, etc. For example, a user can desire to move between two oscillators in the course of a single cutting procedure due to changes in the character of a bone or other factors impacting the desired cutting frequency.

Device 200 can further include a motor, such as an electric motor, and an associated energy supply, not shown, in the form of a rechargeable battery and/or a power supply unit, as well as motor control, switches, etc. for operation and control of a motor or oscillator 204. Motor or oscillator controls can be configured for ease of operation, such as being oriented on housing 202 to align with a typical user's grip or by being remote from the housing, e.g., a foot pedal.

The oscillator 204 can have an associated control mechanism, such as magnet 210. For example, a user can permit or inhibit movement of oscillator 204 by energizing and deenergizing magnet 210 to retain or release a mass associated with oscillator 204. In embodiments, other control mechanisms can also be used. Magnet 210, or other control mechanism, can be energized or deenergized, or otherwise engaged and disengaged, in response to user manipulation of a button or switch, which can be mounted on the housing or remotely located.

The movement of oscillator 204 can be transmitted by drive pin 206 to the dissection head 208. In use, a physician or other user can operate device 200 by placing dissection head 208 against a target, such as portion of bone to be removed to provide a hole for the installation of a pin or screw.

Mass spring system 204 can be initiated, such as by depressing of a button or switch to allow the mass to oscillate on the spring. Oscillation of the mass spring system 204 can drive dissection head 208 to rotate in a first direction, associated with the first direction of oscillation of the mass spring system, and then automatically drive the dissection head 208 to reverse rotational direction and rotate in the reverse direction, associated with the mass of mass spring system 204 reaching the end of its range of motion in the first direction and automatically moving in the other direction. Because dissection head 208 automatically changes direction in this way, any non-target tissue that can be inadvertently captured by motion of dissection head 208, such as by becoming wrapped around the head, will be automatically released when the direction of rotation of the head is reversed, rather than continually pulled in by the continual unidirectional rotation of a conventional drill.

Using mass spring system's 204 natural frequency to drive the movement of dissection head 208, very little power is required to initiate, maintain, or halt motion of dissection head 208 according the needs of the surgeon, or other operator, or the procedure. Little to no power input is necessary to initiate oscillation of mass spring system 204, enabling device 200 to be highly compact due to the integration of either no or only very small batteries or other power supplies. For example, if a physical restraint is used to retain the mass of mass spring system 20 when device 200 is not in operation, then operation can be fully manual and not require any power supply at all for operation. Device 200 can also be fully self-contained, such that no connection to an external power supply is necessary, improving ease of use for the operator, especially given tight constraints on space associated with minimally invasive surgery. In embodiments, power-driven operation can still be desired with size and power requirements reduced but not replaced by power-free initiation of the drive system.

In situations when the operator can need to quickly stop the dissection head 208, for instance due to encountering an unexpected obstacle in drilling, mass spring system 204 can be quickly and effectively halted, thus halting the associated motion dissection head 208, without large power input because there is no need to overcome motor inertia to stop. This allows for a much more minimal braking system then required by conventional motorized drills and other surgical tools.

A wide variety of mass and spring combinations are envisioned to achieve different natural frequencies varying the speed or rotational degree of dissection head 208. The optimum frequency for a particular procedure can depend on a number of factors including, but not limited to, the character of the bone or other tissue to be dissected, the geometry of the dissection tip chosen, the angle of displacement available given the location of the target and any constraints associated with a minimally invasive approach. Further, different architectures are envisioned for transmitting motion from the mass spring system to the dissection head which can permit operators greater control over the range of motion provided by the dissection head. For example, in a first surgery a surgeon might prefer a dissection head which rotates a full 360 degrees in a first direction before oscillating and reversing to rotate a full 360 degrees in the opposite direction and can further desire a high speed of movement from dissection head 208 for rapid dissection of the bone. In a second procedure the surgeon can instead prefer a much smaller range of motion, for example 90 degrees of rotation by the dissection head 208 in a first direction before reversing and rotating 90 degrees in the second direction, and can further desire a lower speed or frequency, giving improved fine control over the amount of bone or other tissue removed and a greater assurance of minimal impact on surrounding tissue.

Figure 5:
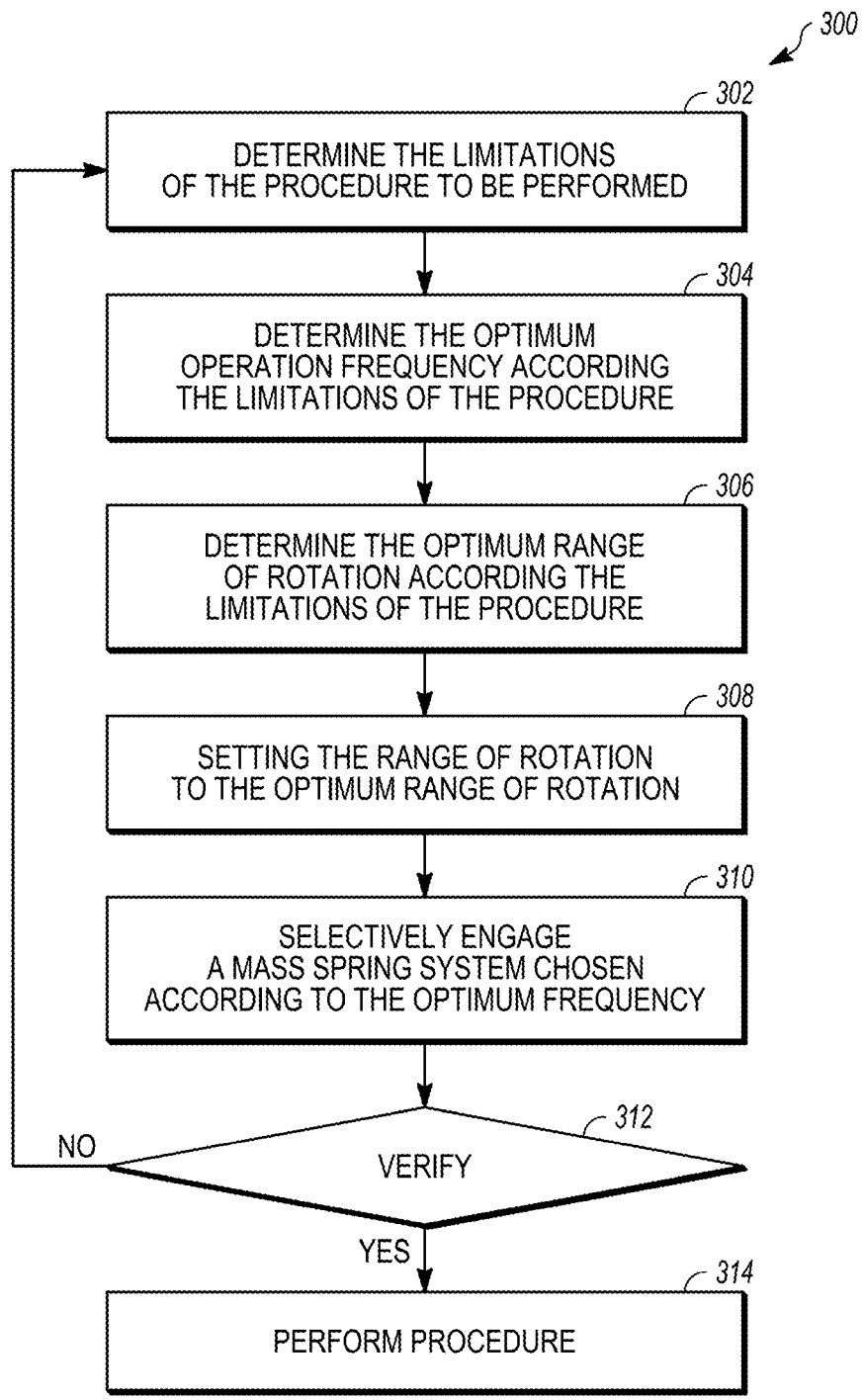
FIG. 5 is a flowchart of an example method of operating a surgical tool with alternating rotational motion, according to embodiments of the present disclosure.

One example method 300 that can be carried out by a surgeon, surgical robot, or other user is shown by the flowchart of FIG. 5. The method 300 can be performed in any order, and in embodiments one or more of the operations depicted and/or described can be removed according to the user's preferences or goals.

In this example, method 300 can begin by determining the specific limitations of the procedure to be performed, as at operation 302. Limitations can include considerations such as the angle of displacement, the character and location of the bone or other tissue to be removed or otherwise cut, the character and arrangement of surrounding tissue, the degree of invasiveness which can be considered acceptable, how much time the surgeon or other use can have to complete the procedure, other risk factors experienced by the patient, etc.

Considering the limitations of the procedure to be performed, the optimum frequency can be determined, as at operation 304. The frequency can generally set the speed of movement and frequency of reversal of the rotational direction of the dissection head. The optimum frequency for a given procedure can vary depending on the limitations of the procedure, as well as other considerations such as the skill of the surgeon or other operator, or the degree of vibrations the mass-spring or other driver can produce as a given frequency.

Considering the limitations of the procedure to be performed, the optimum range of rotation can be determined, as at operation 306. Like frequency, the optimum range of rotation can depend on any of the limitations of the procedure, or other considerations as well. For example, a procedure which must be completed rapidly or involves a target with little surrounding tissue in danger of becoming entangled with the dissection head can be performed using a large range of rotation, e.g., 360 degrees of rotation between reversals. In another example, the target can be porous or have other characteristics which make the target prone to unintended fractures, or the target can be surrounded by tissue which is very likely to be become entangled with the dissection head, such as nerves or blood vessels, in which case the procedure can be performed using a relatively small range of motion, e.g., 60 degrees of rotation between reversals.

In embodiments, the optimum frequency and the optimum range of rotation can be chosen together, as one can impact the other.

The range of rotation of the device can be set to the optimum range of rotation, as at operation 308. The range of rotation can be set by any appropriate means, such as by selection of a particular dissection head, by selection of a particular drive pin configured to drive the dissection head through fixed or variable range of motion, integration of a gearing system, etc.

In embodiments, the range of rotation can be fixed according to the structure of the device or the device can be configured such that the range of rotation can be varied, such as by adjusting a dial or other control, or by integration of a clutch or other means of varying the dissection head, drive pin, or other installed means of controlling range of rotation. For example, a device according the present disclosure can have various interchangeable collars which contain gearing to control the range of rotation of the dissection head.

The frequency of the device can be set to the optimum frequency, such as by selecting a particular mass-spring system with a natural frequency equal to the optimum frequency, as at operation 310. For example, a surgeon or other user can use a kit or set of multiple devices according to the present disclosure, each comprising a single mass-spring driver with a particular natural frequency. The surgeon or other user can then choose from among the kit or set the particular device that operates at the determined optimum frequency.

In embodiments, a device according to the present disclosure can contain multiple mass-spring drivers, each with a different natural frequency, and the surgeon or other operator can choose from among the various drivers by means of a clutch or other mechanism.

The above-described embodiments of the present disclosure can be assembled and adjusted by manual manipulation of the outer surfaces of the components. It will be understood that in this configuration, it is advantageous for the user such that additional instrumentation, tools or intricate movements are not required to accommodate the coupling and adjustment of the various components.

It should be understood that various aspects disclosed herein can be combined in different combinations than the combinations specifically presented in the description and accompanying drawings. It should also be understood that, depending on the example, certain acts or events of any of the processes or methods described herein can be performed in a different sequence, can be added, merged, or left out altogether (e.g., all described acts or events can not be necessary to carry out the techniques). In addition, while certain aspects of this disclosure are described as being performed by a single module or unit for purposes of clarity, it should be understood that the techniques of this disclosure can be performed by a combination of units or modules associated with, for example, a medical device.

In one or more examples, the described techniques can be implemented in hardware, software, firmware, or any combination thereof. If implemented in software, the functions can be stored as one or more instructions or code on a computer-readable medium and executed by a hardware-based processing unit. Computer-readable media can include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions can be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein can refer to any of the foregoing structure or any other physical structure suitable for implementation of the described techniques. Also, the techniques could be fully implemented in one or more circuits or logic elements.

What is claimed is:

1. A surgical instrument, comprising:
   a housing;
   a first harmonic oscillator contained in the housing, the first harmonic oscillator comprising a mass-spring system;
   an output member at least partially received in the housing and configured to be driven by the harmonic oscillator at a natural frequency of the mass-spring system to reversibly rotate about a longitudinal axis in alternating directions;
   a dissection head having an attachment portion configured to be selectively driven in alternating rotational directions by the output member to remove material from a target bone, wherein the dissection head rotates clockwise in response to movement of the mass-spring system in a first direction, and further wherein the dissection head rotates counterclockwise in response to movement of the mass-spring system in a second direction opposite the first direction; and
   a controller operable to initiate and stop the harmonic oscillator.

2. The surgical instrument of claim 1, further comprising a clutch configured to selectively engage the harmonic oscillator with the output member.

3. The surgical instrument of claim 1, further comprising a second harmonic oscillator.

4. The surgical instrument of claim 3, wherein the first harmonic oscillator oscillates at a first natural frequency, the second harmonic oscillator oscillates at a second natural frequency, and the first natural frequency differs from the second natural frequency.

5. The surgical instrument of claim 3, further comprising a first clutch configured to selectively engage the first harmonic oscillator with the output member and a second clutch configured to selectively engage the second harmonic oscillator with the output member.

6. The surgical instrument of claim 1, wherein the harmonic oscillator is configured to oscillate at two or more natural frequencies.

7. The surgical instrument of claim 1, wherein the harmonic oscillator is atorsional oscillator.

8. The surgical instrument of claim 1, wherein the mass-spring system comprises a mass and the mass comprises a magnetic material.

9. The surgical instrument of claim 8, wherein the harmonic oscillator is engaged by applying a magnetic field to the mass.

10. The surgical instrument of claim 1, wherein the mass-spring system comprises a mass and at least two springs, each of the at least two springs having a different stiffness; and
    the harmonic oscillator is configured to oscillate at two or more natural frequencies by selectively engaging the mass with each of the at least two springs.

11. The surgical instrument of claim 1, further comprising a motor.

12. The surgical instrument of claim 11, further comprising a first clutch to selectively engage the harmonic oscillator to drive the output member and a second clutch to selectively engage the motor to drive the output member.

13. A surgical instrument, comprising:
    a housing;
    a motor contained in the housing;
    an output member at least partially received in the housing and configured to be driven by the motor to reversibly rotate about a longitudinal axis in alternating directions;
    a dissection head having an attachment portion configured to be selectively driven in alternating rotational directions by the output member to remove material from a target bone;
    a controller operable to initiate and stop the motor, wherein the output member is configured to be driven by the motor to reversibly rotate about a longitudinal axis in alternating directions by engaging with the motor via a first cam system;
    a second cam system; and
    a first clutch configured to selectively engage the first cam system to drive the output member and a second clutch configured to selectively engage the second cam system to drive the output member.

14. The surgical instrument of claim 13, wherein the first cam system is configured such that the output member reversibly rotates in alternating directions at a first target frequency, the second cam system is configured such that the output member reversibly rotates in alternating directions at a second target frequency, and the first target frequency differs from the second target frequency.

15. The surgical instrument of claim 14, wherein the first cam system is configured such that the output member reversibly rotates in alternating directions a first number of degrees between reversals, the second cam system is configured such that the output member reversible reversibly rotates in alternating directions a second number of degrees between reversals, and the first number of degrees differs from the second number of degrees.

\* \* \* \* \*